(12) United States Patent
Wallberg

(10) Patent No.: US 8,156,202 B2
(45) Date of Patent: Apr. 10, 2012

(54) METHOD AND SYSTEM FOR SHARING DATA BETWEEN RADIOLOGY INFORMATION SYSTEMS

(75) Inventor: Joachim Wallberg, Tyresö (SE)

(73) Assignee: Mawell Scandinavia AB, Kista (SE)

( * ) Notice: Subject to any disclaimer, the term of this patent is extended or adjusted under 35 U.S.C. 154(b) by 91 days.

(21) Appl. No.: 11/943,700

(22) Filed: Nov. 21, 2007

(65) Prior Publication Data

US 2008/0140855 A1 Jun. 12, 2008

(30) Foreign Application Priority Data

Nov. 23, 2006 (SE) ........................................ 0602493

(51) Int. Cl.
*G06F 15/16* (2006.01)
*G06Q 50/00* (2012.01)
*G06Q 10/00* (2012.01)

(52) U.S. Cl. ............ 709/219; 709/217; 709/218; 705/2; 705/3

(58) Field of Classification Search .......... 709/217–219, 709/236; 705/2–3
See application file for complete search history.

(56) References Cited

U.S. PATENT DOCUMENTS

| | | | | |
|---|---|---|---|---|
| 5,655,084 A * | 8/1997 | Pinsky et al. | ...................... | 705/3 |
| 5,924,074 A * | 7/1999 | Evans | ............................... | 705/3 |
| 6,031,516 A * | 2/2000 | Leiper | ........................... | 345/629 |
| 6,260,021 B1 * | 7/2001 | Wong et al. | ........................ | 705/2 |
| 6,401,138 B1 * | 6/2002 | Judge et al. | .................... | 719/328 |
| 6,988,075 B1 * | 1/2006 | Hacker | .............................. | 705/3 |
| 7,234,064 B2 * | 6/2007 | Menschik et al. | ............ | 713/193 |
| 7,376,155 B2 * | 5/2008 | Ahn et al. | ....................... | 370/503 |
| 7,523,505 B2 * | 4/2009 | Menschik et al. | .............. | 726/26 |
| 7,853,621 B2 * | 12/2010 | Guo | ............................... | 707/803 |
| 7,925,759 B2 * | 4/2011 | Slik et al. | ....................... | 709/226 |
| 2002/0016718 A1 * | 2/2002 | Rothschild et al. | ............... | 705/2 |
| 2002/0103811 A1 * | 8/2002 | Fankhauser et al. | ....... | 707/104.1 |
| 2003/0187698 A1 | 10/2003 | Bonissone et al. | | |
| 2003/0202087 A1 * | 10/2003 | Izumi et al. | ................ | 348/14.02 |
| 2004/0034550 A1 * | 2/2004 | Menschik et al. | ................ | 705/3 |
| 2006/0206523 A1 * | 9/2006 | Gaurav et al. | .............. | 707/104.1 |
| 2007/0274585 A1 * | 11/2007 | Zhang et al. | .................. | 382/132 |
| 2007/0276789 A1 * | 11/2007 | Keithley et al. | ................... | 707/2 |

FOREIGN PATENT DOCUMENTS

WO WO 01/35310 5/2001

* cited by examiner

*Primary Examiner* — Ashok Patel
*Assistant Examiner* — Linglan Edwards
(74) *Attorney, Agent, or Firm* — Merchant & Gould P.C.

(57) ABSTRACT

The present invention relates to a method and a system for sharing and exchanging event data between at least two 5 radiology information systems. An event in any of the radiology information systems triggers a send and receive server to convert the event data from the radiology information system that has sent out the trigger signal. The send and receive server than then packages the converted 10 data and sends the converted and packed data from the send and receive server to a central server. The central server tags the received data and stores the received data at a central storage unit connected to the central server. Finally, the central server sends the stored data back to 15 any of the radiology information systems via the send and receive server at the request by any of the radiology information systems and if the stored data comprises images exchange the exciting meta-data with meta-data generated by the send and receive server (8) of the receiving radiology 20 information system (2).

10 Claims, 3 Drawing Sheets

METHOD AND SYSTEM FOR SHARING DATA BETWEEN RADIOLOGY INFORMATION SYSTEMS

TECHNICAL FIELD

Figure 1:
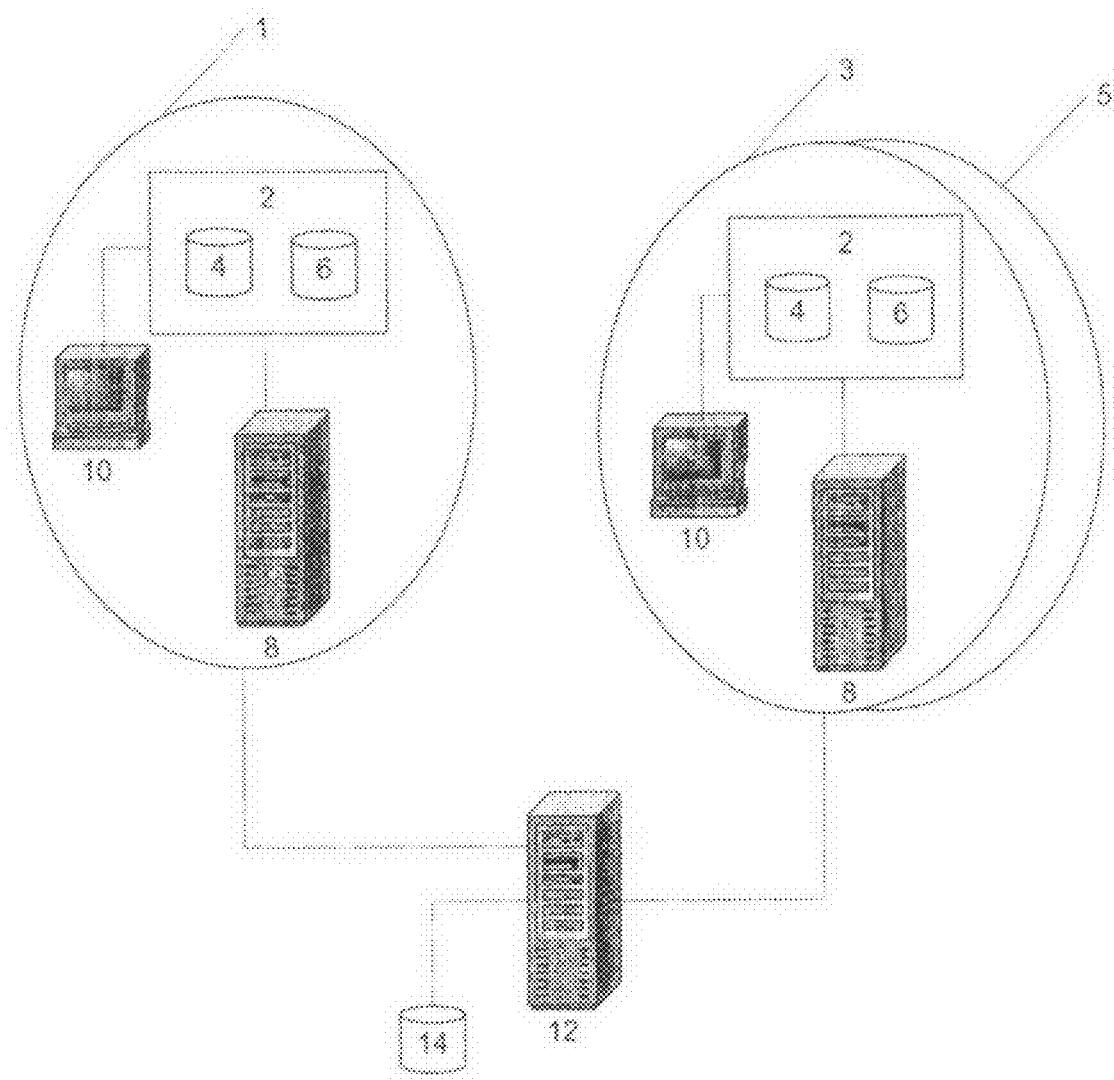

The present invention relates to a method and a system for sharing data between at least two radiology information systems.

PRIOR ART

Today there exist a lot of radiology information systems, which help and support the people working with radiology. This is sufficient as long as one hospital works with its own radiology data. However, if a group of hospitals or different sites at a hospital want to work more closely together with each other and coordinate their work and learn from each other's experience they have to start sharing data with each other. Since, there are different radiology information systems on the market they will not always talk easily with each other. If two different radiology information systems have to talk to each other it is not a major problem. Each radiology information system can be set up such as it can communicate with the other. However, the problem grows with the number of radiology information systems that have to be set up. If there are six different radiology information systems that are to be able to talk to each other each radiology information system must be set up with five separate connections in order to talk to the others. Thus, it is easy to see that this will require a lot of effort as the number of radiology information systems increase.

Today, there are therefore not so many radiology information systems that are connected to each other. The drawback is that the overall resources are not used efficiently. For example, if the workload at one hospital is high it has to deal with the problem itself, even if there are resources available at another hospital.

Another drawback is that the only way that you easily can get a second opinion is from someone working within your own system. Sharing of experience between different hospitals is of course also difficult.

US Patent application 2003/0187698 discloses a method and an apparatus for providing fully integrated information processing, management and communication functions in a fully integrated RIS-PACS system (Radiology Information System-Picture Archive and Communication System). This is an example of a type of radiology information system that can be interconnected with another radiology information system in accordance with what has been described above.

WO 0135310 discloses a method and a system for storing and accessing digital medical images. The system is set up in such a way that participating institutions can access data from a central database. This will work fine as long as all participating institutions show the medical images in the same format. The problem when it comes to showing images on radiology information systems is not so much the showing of the image itself but the meta-data that is incorporated in the image. Even if the meta-data itself may be the same it is often presented differently in different radiology information systems. This can cause a problem for the radiologist when interpreting the image together with the meta-data.

In context of the present invention the term radiology information system should be interpreted in a broad sense, thus including all the systems used in the radiology information system at the hospital, such as the RIS and the PACS.

SUMMARY OF THE INVENTION

The object of the present invention is to provide a method for sharing and exchanging event data between different radiology information systems.

The object of the invention is achieved by a method for sharing and exchanging event data between at least two radiology information systems, in which a trigger signal from any of the radiology information systems is initiated by the occurrence of an event such as a referral or a report registered in the radiology information system. The 25 trigger signal is sent to a send and receive server, which converts the event data from the radiology information system that has sent out the trigger signal. The send and receive server than packages the converted data at the send and receive server and sends the converted and packed data 30 from the send and receive server to a central server. The central server tags the received data and stores the received data at a central storage unit connected to the central server. Finally, the central server sends the stored data back to any of the radiology information systems via the send and receive server at the request by any of the radiology information systems and if the stored 5 data comprises images exchange the existing meta-data with meta-data generated by the send and receive server of the receiving radiology information system.

A more specific object of the invention is to provide a system for sharing and exchanging event data, comprising at least two radiology information systems, a send and receive server connected to each radiology information system, a central server connected to each send and receive server and a central storage unit connected to the central server. The system is configured to perform the method as described above.

An advantage with the method and system according to the invention is that different radiology information systems are able to communicate with each other regardless of the type of system and regardless of how the meta-data associated with the images is organized. There is no longer any need for setting up system to system connections since the method and system according to the invention uses a single node through which one radiology information system communicates with other radiology information systems.

A further advantage is that the method and system enables workload balancing between different hospitals, without a lot of time-consuming user involvement.

SHORT DESCRIPTION OF THE DRAWINGS

Figure 2:
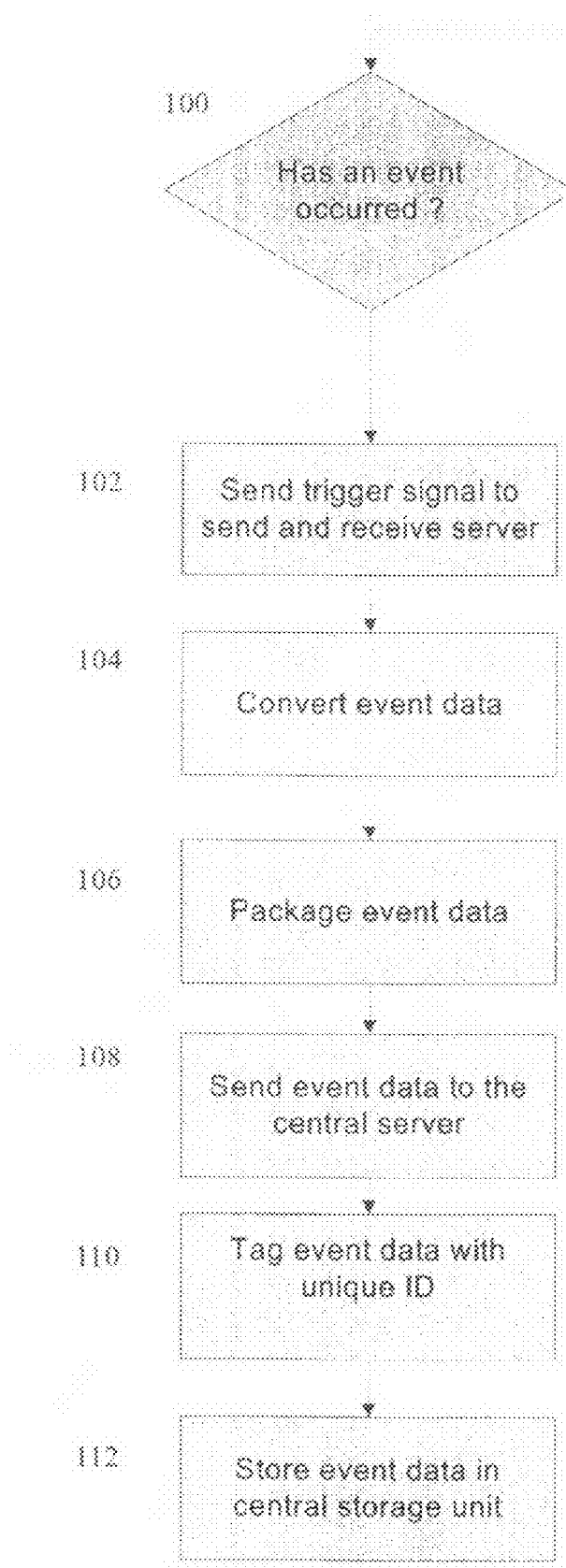
Figure 3:
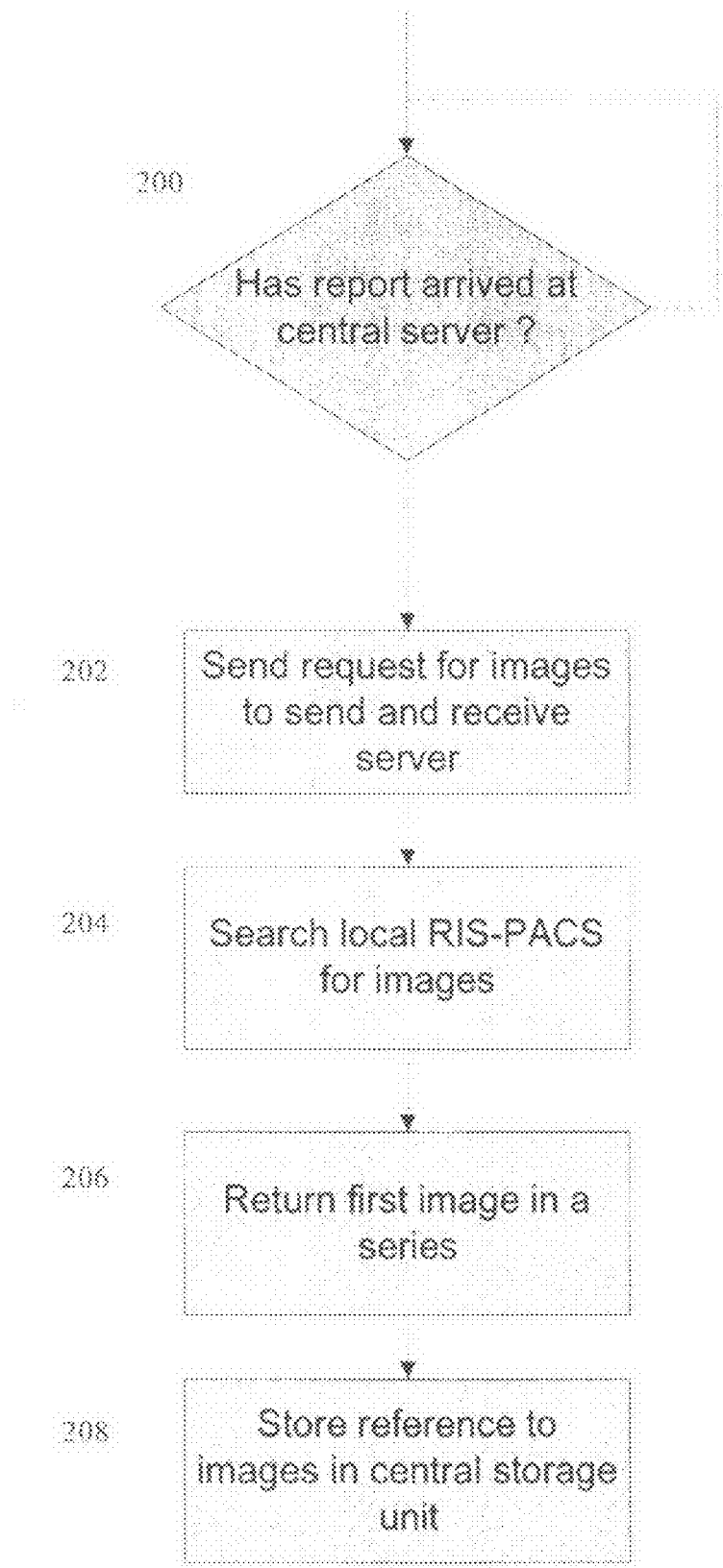

The invention is described in the following with reference to the accompanying drawings, in which FIG. 1 is a schematic view of the virtual radiology information system according to the invention, FIG. 2 and FIG. 3 show a flow chart of the method for sharing and exchanging data according to invention.

DETAILED DESCRIPTION OF THE INVENTION

FIG. 1 shows a schematic view of the virtual radiology information system according to the invention. The radiology system at one hospital or department 1 comprises a RIS-PACS system 2, having the RIS database 4 and the PACS database 6. To access the information in the RIS-PACS system 2 an ordinary workstation 10 is connected thereto. Furthermore, the RIS-PACS system 2 is connected to a send and receive server 8, which enables the RIS-PACS system 2 to communicate with the outside world. The outside world in this case is other hospitals or departments 3 and 5. The radiology departments 3 and 5 are set up in a similar way as the radiology department 1. A central server 12 interconnects the different hospitals or departments 1, 3 and 5. A central storage unit 14 is connected to central the server 12.

The above mentioned system, configured to perform the method according to the invention, constitutes a virtual radiology information system in which stored information in one RIS-PACS system 2 can be shared and exchanged. One great benefit of this virtual system is that resources no longer have to be seen as local, but instead can be global. How this is done will be described hereinafter.

FIG. 2 shows a flow chart of the method according to the invention. The method starts at 100 waiting for an event to occur in the RIS-PACS system 2. In context of this description an event can be anything that changes the information stored in the RIS-PACS system 2. Examples of events are referrals and reports written and entered into the system 2 by a radiologist. As long as no event occurs the method keeps on waiting for something to occur.

Now, when the X-ray department receives a referral from a referring doctor the patient will be booked in the RIS-PACS system 2 and this booking will trigger the start of the method by sending a trigger signal at 102 to the send and receive server 8, which is the communication gateway of the RIS-PACS system 2. The send and receive server 8 is connected to the hospital's IT-network and is of course protected by a firewall. The send and receive server can be any server as long as it is configured to perform the method according to the invention.

After receiving the trigger signal the send and receive server 8 will convert the referral data to standardized XML format at 104. However, it shall be understood that the data can be converted to any suitable language, the important thing being that all data is converted to a common language to enhance the sharing and exchanging of data between the different RIS-PACS systems 2. This converting especially enhances the possibility to show meta-data associated with an image in the same way as the RIS-PACS system 2 in question always does and not in the way that the RIS-PACS system 2 that saved the meta-data is doing.

The send and receive server 8 than packages the converted data at 106. By packaging is meant to make a package of the data that can be sent to the central server 12 in a safe way without being read by anyone who is not authorized. Thus in this example the send and receive server 8 encrypts the XML using a X509 certificate as part of the packaging.

The converted and packed data is then sent from the send and receive server 8 to the central server 12 at 108. The central server 12 tags the received data, i.e. gives the referral a unique ID at 110. The central server 12 than stores the tagged data in a central storage unit 14 connected to the central server at 112. The central server 12 can be any server as long as it is configured to perform the method according to the invention.

The central server 12 now has a copy of a referral which is accessible from all RIS-PACS systems 2 that are connected to the central server 12 via a send and a receive server 8. Upon a request from any of the RIS-PACS systems 2 the central server 12 will be able to send the data for this specific referral to the requesting RIS-PACS system 2.

The above described method is also applicable if the radiologist writes a report in the RIS-PACS system 2. Thus, the same steps will be taken in order to save the report at the central storage unit 14 connected to the central server 12.

FIG. 3 shows another flow chart of a preferred embodiment of the invention. The method starts at 200 where the central server 12 is waiting for receiving a report written by the radiologist. When a report is received the central server 12 will send a request to the local send and receive server 8 and ask if there are any images that belong to this report at 202. The send and receive server 8 will send a query to the local RIS-PACS system 2 that will search the system 2 for said images at 204. If the images are found the first image in a series will be returned to the central server 12 at 206. The central server 12 will store a reference to the images of the report in the central storage unit 14 at 208. Thus, the central server 12 now holds a reference to the images of the report together with the referral and a pointer towards the images.

If, for example, another hospital now wants access to these images in order to do an evaluation thereof the following will happen. Firstly, the hospital or department, which produced the images, writes a referral in its own RIS-PACS system 2, asking another hospital to do the evaluation of the images. The steps describing the referral in conjunction with FIG. 2 will be performed, i.e. the patient will be booked in the RIS-PACS system 2 and the referral will end up in the central storage unit 14.

Secondly, the receiving hospital will get notified that it shall perform an evaluation on the specified images. In this example the PACS systems 6 storing the images are not the same for the two hospitals. Actually, the images are the same, but the meta-data contained therein are arranged differently, which makes it difficult for the receiving hospital to read. Thus, according to the present invention the following steps will be performed in order to solve this problem.

Upon receiving the notification the receiving hospital, if they accept the referral, will book the patient in the RIS-PACS system 2 and generate meta-data according to the standards of their own PACS system 6. The acceptance of the receiving hospital will also trigger the sending of the images from the sending hospital and the storing in the central storage unit 14. At the sending and receiving server 8 the images are now available as a virtual modality having the correct meta-data. When the receiving hospital makes a call for the images they are imported from a regular modality, i.e. the central storage unit 14 connected to the central server 12. When the images are imported the local send and receive server will exchange the existing meta-data with its own generated meta-data. Thus, the systems ability to work with virtual modality will considerable enhance the exchange of images and its associated meta-data between different systems.

As can be understood by the above description the method according to the invention will be really valuable in making the work at a radiology department more effective and automated. Once the data can be stored at a central point and is easily accessible from all RIS-PACS systems 2 connected thereto it will be easy to share and exchange data. Especially, the feature to automatically exchange meta-data will be useful, since this is down manually today.

One other example is the redirecting of a referral. If a radiology department has too much work and are not able to carry out all the referrals they can connect to the central server 12 from any workstation 10 connected to the system. And as shown above the central server 12 holds copies of all referrals with references to images if there are any. The referral or referrals which one wants to send away due to the workload is/are selected together with a receiver. The receiver can be an individual, a department or also be an examining pool.

The central server 12 sends a request to the send and receive server 8 at the local RIS-PACS system 2, asking for the stored images belonging to the referral to be redirected.

The send and receive server 8 packages the images to a single file and sends them to the central server 12, which stores the file in the central storage unit 14 and then notifies the receiving person or unit about the redirected referral.

The notification can be done in any suitable way, i.e. with SMS via telephone, via fax or e-mail etc. The receiver uses a workstation 2 connected to the system to connect to the central server 12 and accepts, revokes or puts the referral on hold. An accept triggers the sending of images, referral and report if any to the accepting unit or person. Thus, without having a new appointment the patient is rebooked to a new resource and the only human involvement has been the cancelling of a referral in one RIS-PACS system 2 and the accepting of the referral in another RIS-PACS system 2.

Thus, the method according to the present invention will substantially influence the effectiveness of how radiology work is performed.

The great benefit of the method and system according to the invention is the central storage of all the data that makes is possible for all connected units to access data if they are authorized. Furthermore, the conversion of the data before it is stored centrally also makes it possible to present the meta-data in the same way that it is always presented on that specific system. Thus, the meta-data may always be presented in a way that the radiologist is used to regardless of how the meta-data was originally stored. Thus, changes of the data will be readily available for all without any hazels or delays.

It shall be understood that even if the invention has been described with reference to preferred embodiments the invention is not limited thereto. There are many other embodiments and variations that are likewise within the scope of the invention, which is best defined by the accompanying claims.

The invention claimed is:

1. A method for sharing and exchanging event data between different types of radiology information systems having different data organizations, wherein each radiology information system has an associated arrangement for presenting meta-data displayable with images that is different from an associated arrangement of at least one other radiology information system, the method comprising the steps of:
   sending out a trigger signal from any of the radiology information systems to a send and receive server at the occurrence of an event in any of the radiology information systems,
   converting the event data from the radiology information system that sent out the trigger signal at the send and receive server,
   packaging the converted data at the send and receive server,
   sending the converted and packed data from the send and receive server to a central server,
   tagging the received data at the central server,
   storing the received data at a central storage unit connected to the central server, and
   sending the stored data back to any of the different radiology information systems via the central server and the send and receive server at the request by any of the radiology information systems; and
   exchanging the meta-data displayable with the image at the radiology information system that sent out the trigger signal with meta-data generated by a send and receive server of a receiving radiology information system to provide exchanged meta-data at the receiving radiology information system having a different data organization compared to the meta-data displayable with the image at the radiology information system that sent out the trigger signal; and
   presenting the exchanged meta-data displayable with the image in the receiving radiology information system with the associated arrangement of the receiving radiology information system, the receiving radiology information system being of a different type as compared to the radiology information system that sent out the trigger signal.

2. A method according to claim 1, further wherein the triggering occurrence is a referral and that the triggering is initiated by booking a referral in any of the radiology information systems.

3. A method according to claim 1, further wherein the triggering occurrence is a report and that the triggering is initiated by writing a report in any of the radiology information systems.

4. A method according to claim 3, further wherein the central server upon receiving a report initiates the steps of:
   sending a request to the send and receive server at the local radiology information system that issued the report, asking if there are any stored images belonging to the report,
   searching the local radiology information system for said images and if found returning the first image in a series to the central server, and
   storing a reference to the images of the report in the central storage unit connected to the central server.

5. A method according to claim 4, further wherein redirecting a referral comprising the following steps:
   selecting a referral to be redirected and its associated reference to the images,
   sending a request from the central server to the send and receive server at the local radiology information system, asking for the stored images belonging to the referral to be redirected,
   packaging the images to a single file and sending them to the central server,
   storing the file in the central storage unit connected to the central server, and
   notifying the person that is going to receive the redirected referral.

6. A computer program comprising non-transitory code means stored on a central server for performing the steps of claim 1, when the program is run on a computer.

7. A computer program product comprising non-transitory program code means stored on a central server for performing the method of claim 1, when said product is run on a computer.

8. A radiology information system for sharing and exchanging event data, comprising:
   at least two different types of radiology information systems having different data organizations, wherein each of the different types of radiology information system has an associated arrangement for presenting meta-data displayable with images that is different from an associated arrangement of at least one other radiology information system;
   a send and receive server connected to each radiology information system; and
   a central server connected to each send and receive server and a central storage unit connected to the central server;
   wherein the at least two different types of radiology information systems are configured to send out a trigger signal to the send and receive server at the occurrence of an event in any of the radiology information systems,
   wherein the send and receive server is configured to:
      convert the event data from the radiology information system that sent out the trigger signal,
      package the converted data, and send the converted and packed data to the central server, wherein the central server is configured to:

tag the received data, store the received data at the central storage unit connected to the central server, and send the stored data back to any of the different radiology information systems via the send and receive server at the request by any of the radiology information systems;

wherein the system is further configured to exchange the meta-data displayable with an image at the radiology information system that sent out the trigger signal with meta-data that is generated by a send and receive server of the receiving radiology information system to provide exchanged meta-data at the receiving radiology information system having a different data organization compared to the meta-data displayable with the image at the radiology information system that sent out the trigger signal; and present the exchanged meta-data displayable with the image in the receiving radiology information system with the associated arrangement of the receiving radiology information system, the receiving radiology information system being of a different type as compared to the radiology information system that sent out the trigger signal.

9. A system according to claim 8, wherein the system, upon receipt of a report at the central server:

sends a request to the send and receive server at the local radiology information system that issued the report, asking if there are any stored images belonging to the report, searches the local radiology information system for said images and if found returning the first image in a series to the central server, and stores a reference to the images of the report in the central storage unit connected to the central server.

10. A system according to claim 9, wherein the system, is configured for redirecting a referral by:

selecting the referral to be redirected and its associated reference to the images, sending a request from the central server to the send and receive server at the local radiology information system, asking for the stored images belonging to the referral to be redirected, packaging the images to a single file and sending them to the central server, storing the file in the central storage unit connected to the central server, and notifying the person that is going to receive the redirected referral.

* * * * *